US00PP30129P3

(12) United States Plant Patent
Orton et al.

(10) Patent No.: US PP30,129 P3
(45) Date of Patent: Jan. 22, 2019

(54) ***ILEX* INTERSPECIFIC HYBRID NAMED 'CR195-115'**

(50) Latin Name: ***Ilex* interspecific hybrid**
Varietal Denomination: CR195-115

(71) Applicant: RUTGERS, THE STATE UNIVERSITY OF NEW JERSEY, New Brunswick, NJ (US)

(72) Inventors: Elwin R. Orton, Millstone, NJ (US); Thomas J. Molnar, New Brunswick, NJ (US)

(73) Assignee: Rutgers, The State University of New Jersey, New Brunswick, NJ (US)

( * ) Notice: Subject to any disclaimer, the term of this patent is extended or adjusted under 35 U.S.C. 154(b) by 0 days.

(21) Appl. No.: 15/530,644

(22) Filed: Feb. 13, 2017

(65) Prior Publication Data

US 2018/0235129 P1 Aug. 16, 2018

(51) Int. Cl.
*A01H 5/00* (2018.01)
*A01H 6/00* (2018.01)
*A01H 5/12* (2018.01)

(52) U.S. Cl.
USPC ..... Plt./247
CPC ..... *A01H 6/00* (2018.05); *A01H 5/12* (2013.01)

(58) Field of Classification Search
USPC ..... Plt./247
CPC ... A01H 5/12; A01H 5/02; A01H 5/00; A01H 5/08; A01H 6/00
See application file for complete search history.

(56) References Cited

PUBLICATIONS

JC Raulston Arboretum at NC State University, JC Raulston Arboretum Plant Sale 2016, retrieved on Mar. 7, 2018, retrieved from the Internet at https://jcra.ncsu.edu/horticulture/sales/plant-sale/index.php?year=2016, 2 pp. (Year: 2016).*
Patti O, retrieved on Mar. 7, 2018, retrieved from the Internet at http://tmsearch.uspto.gov/bin/showfield?f=doc&state=4801:hp1ita.3.1, 2 pp. (Year: 2018).*

* cited by examiner

*Primary Examiner* — June Hwu
(74) *Attorney, Agent, or Firm* — Patrick J. Daugherty; Daugherty & Del Zoppo Co., LPA

(57) ABSTRACT

'CR195-115' is a new and distinct cultivar of interspecific, hybrid evergreen holly distinguished by its small spineless leaves and narrowly conical single-trunk tree form, which is highly dissimilar to other forms of *Ilex*. Its parentage includes four species (*Ilex crenata, I. aquifolium, I. pernyi*, and *I. rugosa*), further distinguishing it from other cultivars. Plants are winter-hardy in USDA Hardiness Zone 6b and exhibit a moderate rate of growth, develop an upright, densely-branched narrow conical form of compact size, and produce an abundance of well-displayed shiny black fruit.

3 Drawing Sheets

Latin name of genus and species of the plant claimed: *Ilex* interspecific hybrid.

Variety denomination: 'CR195-115'.

CROSS REFERENCE TO RELATED APPLICATIONS

NONE

STATEMENT REGARDING FEDERALLY SPONSORED RESEARCH OR DEVELOPMENT

NONE

Description

Botanical designation: *Ilex crenata* x (*Ilex* x *aquipernyi* x *Ilex rugosa*)

BACKGROUND OF THE INVENTION

This new cultivar is the product of a long standing program of hybridization and selection of interspecific hybrid hollies (*Ilex*) at a location in New Brunswick, N.J.; in this instance, it is the result of a controlled cross of *Ilex*

*crenata* 'Sky Pencil' with *Ilex* x 'Jersey Jewel' (*I.* x *aquipernyi* x *I. rugosa*). Our breeding objective was to create an evergreen holly with a desirable and unique upright and compact tree form and other characteristics which would make it commercially attractive with the potential for wide distribution. We believe that we have been successful in achieving this goal. Further, to our knowledge, plants of these four species combination have not been reported previously.

We selected the particular seedling hereof from known progeny grown in a cultivated area, and as a result, have in turn caused the same to be asexually reproduced by the rooting of stem cuttings. The reproduction, growth, and selection of the new cultivar and its asexually propagated clones took place in the vicinity of Adelphia, Millstone, and New Brunswick, N.J. The claimed cultivar is stable and reproducible true-to-type in successive generations of asexual reproduction.

The description which follows will be understood as clearly defining the new cultivar, the desirable characteristics of which are the result of such a program as has been heretofore stated.

SUMMARY OF THE INVENTION

Our invention, designated here as 'CR195-115', is a novel, unique, and highly ornamental form of interspecific hybrid *Ilex* which originated by crossing *Ilex crenata* 'Sky Pencil' (unpatented) with *Ilex* x 'Jersey Jewel' (unpatented). 'Jersey Jewel' is the result of a cross of *I.* x *aquipernyi* 'San Jose' x *I. rugosa* R9-1 (PI 276084). The new cultivar was derived from a controlled pollination made in June, 1992. The seed was harvested that same year and germinated in April, 1993. The resulting seedling was transplanted to progressively larger containers and was finally transplanted to the field at a Research and Extension Farm in Adelphia, Monmouth County, N.J. in 1996 in the location of Field 71, Row 31, Plant 7. The original seedling of 'CR195-115', tested under the identification code of CR195-115, was asexually propagated in 2001 and subsequently tested in New Brunswick and Millstone, N.J., and shown to be true-to-type.

The new cultivar exhibits the following combination of traits: (a) a moderately vigorous, dense, and self-compacting evergreen tree with a single trunk and very upright, narrowly conical form of much less width and depth than that of all forms of *Ilex crenata* known to us; (b) small, non-spiny *I. crenata*-like evergreen leaves that are primarily obovate with a rounded base, serrate margin, and obtuse apices; (c) an abundance of pistillate flowers well positioned on shoots of the previous year's growth that provide a well distributed and consistently abundant set of fruit that matures to a shiny black color in the early fall and then persisting throughout the winter; (d) winter hardiness in New Jersey (USDA hardiness Zone 6b); and (e) low susceptibility to disease and insect pests.

In a production environment, plants of 'CR195-115' develop an upright, dense, self-compacting, narrowly-conical growth habit with single trunk and strong apical dominance without corrective pruning. Their tall, narrow stature relative to the broader tree form typical of plants of *I. crenata* makes them useful in a wider range of landscape settings. It is clearly distinguished from its parent 'Jersey Jewel' based on its contrasting single trunk, upright narrowly conical growing habit ('Jersey Jewel' is a small-statured, dwarf plant with compact short growth best suited for rock gardens and bonsai applications) and from patented and/or commercially available cultivars of upright *I. crenata* and other *Ilex* interspecific hybrids with somewhat similar plant forms in the following respects:

Plants of the 'CR195-115' are very narrowly conical in growth habit with a tall single leader whereas plants of *I. crenata* 'Sky Pencil' (not patented) are narrowly columnar in plant form typically with multiple leaders. 'CR195-115' is also much taller as a mature plant than 'Sky Pencil' ('CR195-115' reaches 3.63 m at 15 years). The leaves of 'Sky Pencil' are also longer and wider than those of 'CR195-115'.

'CR195-115' differs from *I. crenata* 'Steeds' (not patented) by being much more narrowly conical and tall, whereas 'Steeds' is broadly conical being wider at all points of growth from base to apex. 'Steeds', a male holly, lacks a fruit display and also has larger leaves in both length and width that are a slightly darker green color and are glossier than those of 'CR195-115'.

'Rutholl' (U.S. Plant Pat. No. 23,905 P2), Trademark name Emerald Colonnade®, is a male plant (has no fruit display). 'Rutholl' is much wider than 'CR195-115' in growth habit (somewhat broadly conical), also being widest at the central area of the plant, with a rounded base and conical apex, whereas 'CR195-115' is widest near its base and narrowly conical throughout with a very narrow apex. Leaves of 'Rutholl' are longer and wider than those of 'CR195-115'.

'Farrowone' (U.S. Plant Pat. No. 20,049 P2), Trademark name Sky Pointer®, has leaves that are longer than 'CR195-115' although similar in width. 'Farrowone' is not known to produce fruit, whereas 'CR195-115' produces large amounts of well-displayed black fruit even on young trees (only one or two years from a rooted cutting from a mature tree). 'FarrowSK6' (U.S. Plant Pat. No. 25,852 P2), Trademark name Patti O®, has slightly smaller leaves on average in both length and width than 'CR195-115'. However, like 'Farrowone' there is no fruit display observed on plants of 'FarrowSK6', whereas 'CR195-115' produces abundant fruit.

BRIEF DESCRIPTIONS OF THE DRAWINGS

FIG. 1 on the left was taken in July and FIG. 1 on the right taken in November.

Figure 1:
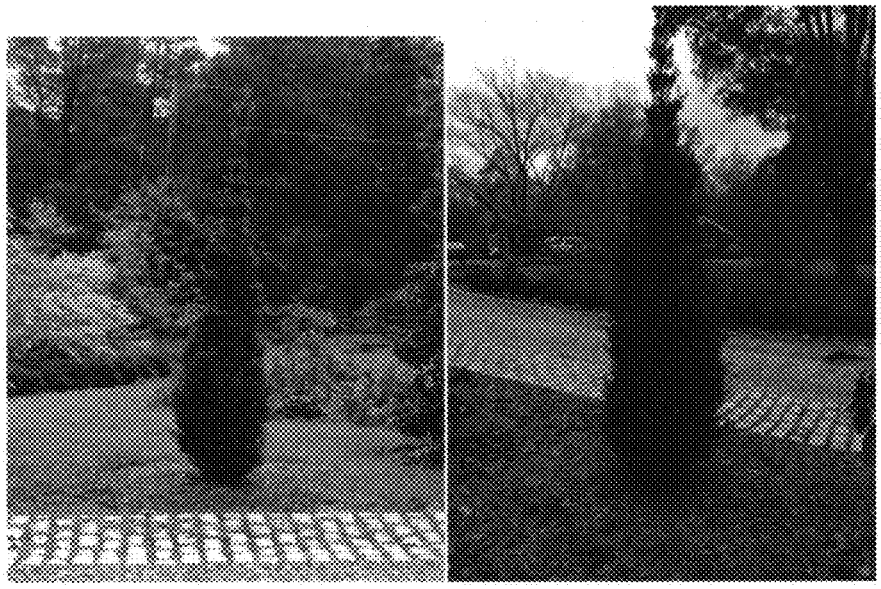
FIG. 1 illustrates the growth habit of a 15-year-old plant.
Figure 2:
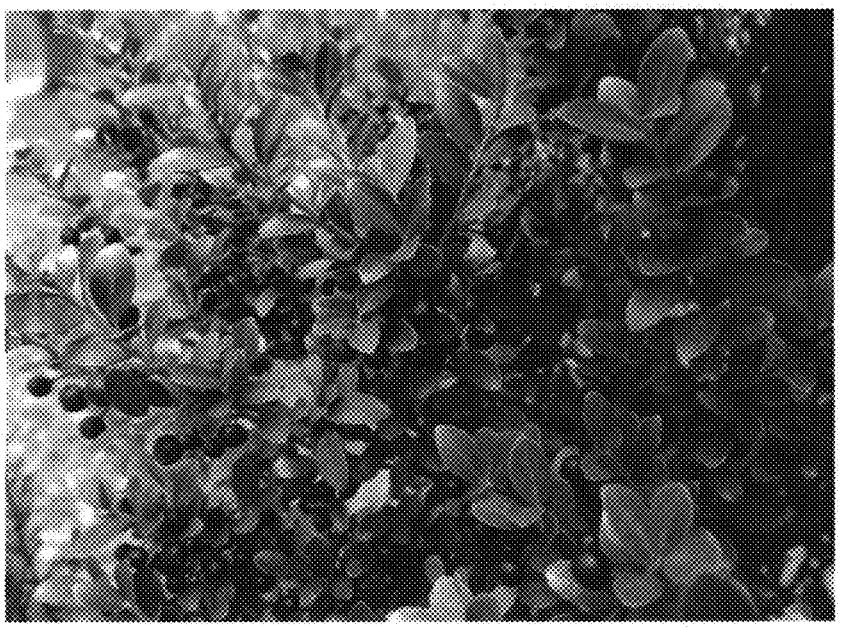
FIG. 2 illustrates typical leaves and fruit display of the new cultivar in November.
Figure 3:
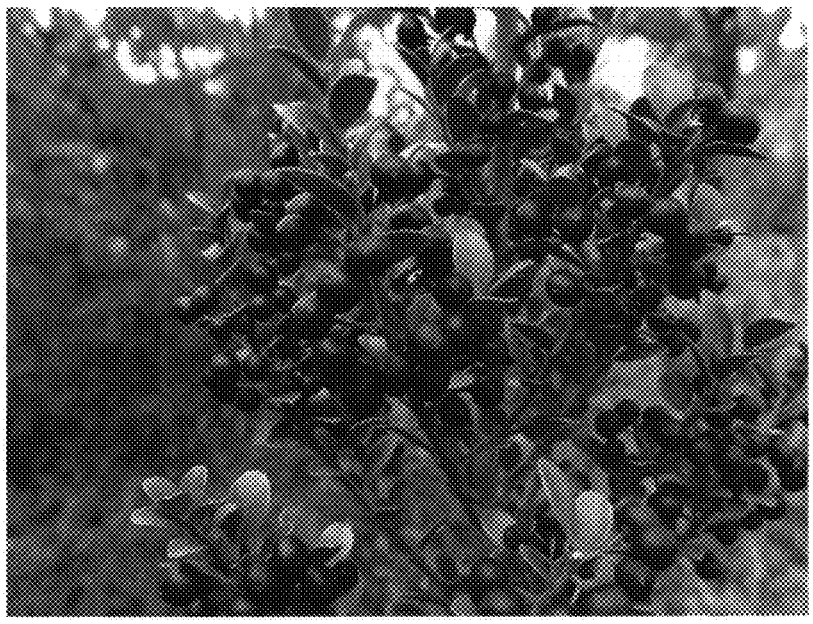
FIG. 3 is a close up of heavy fruit production on 4-year-old cutting-produced plant in November.

The color definitions in the specification have been taken from The R.H.S. Colour Chart (1966) of The Royal Horticultural Society, London, England. The colors depicted are believed to be of a high level of color fidelity and are believed to be as close to the actual coloration of the plant as possible in a photographic illustration of this quality. However, due to factors such as light reflectance, cultural conditions, and horticultural practices, the coloration of this plant should be understood to be approximate. For example, the leaf color may vary depending on the composition and the concentration of fertilizer applied to the plant.

BOTANICAL DESCRIPTION OF THE PLANT

The following is a detailed description of our new cultivar of interspecific hybrid *Ilex* made from observation of a 15-year-old cutting-grown plant existing in the vicinity of Millstone, N.J.

Parentage: *Ilex crenata* 'Sky Pencil' x 'Jersey Jewel' (*I.* x *aquipernyi* 'San Jose' x *I. rugosa* H9-1).

Pollinator: can be pollinated by a staminate plant of either *Ilex crenata, Ilex aquifolium, Ilex pernyi, Ilex rugosa, Ilex* x *aquipernyi*, or *Ilex* x *meserveae* with a synchronous flowering period.

Plant growth characteristics: Plants have an upright, narrowly conical habit with 15-year field-grown plants attaining a size of 3.63 m in height and 1.1 m in width at its widest point (0.76 m from ground) under conditions of minimal fertilization and minimal supplemental irrigation. Plants establish a dominant central trunk, and branching is dense and self-compacting with very little or no pruning. The diameter of the tree trunk of a 15-year-old plant at 10 cm above the soil level is 14.0 cm. The bark texture of the trunk is smooth and the color is Greyed-Green Group 197B close to the base, lightening to Greyed-Green Group 197C higher up on the trunk. Plants bear abundant crops of black berries annually which are well displayed among the green to light-green, slightly serrate leaves which retain their color even when bearing a heavy crop of fruit.

A plant in the mature phase (flowering) can be achieved in one year from a rooted cutting taken from a plant in the mature phase. The subsequent annual growth rate ranges from 20-30 cm for plants grown in full sun, varying as indicated depending on climatic conditions, soil or growing medium type, and cultural practices such as fertilization and irrigation. Our studies showed that cuttings rooted in January with bottom heat, intermittent mist, and 0.8% IBA powder reached an average of 61 cm tall and 27 cm wide (near bottom ¼ of plant) (n=40) by July of the third growing season (30 months). Field planted six-year-old cuttings grown in full sun reached an average height of 2.32 m and a width of 0.30 m (n=7).

Foliage:

*Type*.—Evergreen, coriaceous (abaxial and adaxial), alternate, primarily obovate with rounded base, serrate margin, and obtuse apices. Prominent stomata underneath (visible punctate effect under handlens magnification); venation underneath with invisible secondary and tertiary veins, midvein raised; leaf margin slightly recurved, entire except for small, separated teeth, 6-9 per side, 0.2-0.3 mm long; leaf teeth deciduous with age.

*Size*.—Leaf size varies slightly with light intensity and fertility program where plants are growing. Size is generally in the range of 10-18 mm long and 6-9 mm wide.

*Petiole*.—Approximately 2.0-2.4 mm long and 0.8-1.0 mm wide, color is closest to Yellow-Green Group 146C.

*Color*.—Mature growth, upper surface — closest to between Green Group 137A and 137B; lower surface — Yellow-Green Group 146B. New growth, upper surface — closest to Yellow-Green Group 146C; lower surface — closest to Yellow-Green Group 144A.

Stems:

*Color*.—New growth in spring and summer is closest to Yellow-Green Group 144A. One-year-old stems are closest to Yellow-Green Group 146B and 146C; older branches and the central stem are primarily Greyed-Green Group 197B, and the base of the tree trunk is closest to Greyed-Green Group 197C. Numerous, dense, tightly angled branches, typically angled around 55-65°. Current season's growth is 2.5-3.5 mm in diameter. One-year-old branch is typically 8.0 to 15.0 cm in length and 3.0-4.0 mm in diameter. Older wood is progressively larger in diameter. Pubescence present as small, white hairs on branches, pedicels, and petioles.

Inflorescence:

*Inflorescence*.—2-3-flowered, axillary, cymose. Dormant flower bud is ovoid in shape, approximately 2.0 mm tall and 1.0 mm wide, and placed on 3.5 to 4.0 mm high peduncles (1.0 mm wide) both the color of Green Group 137 B. As flower buds start to expand and break dormancy, color lightens to between Yellow-Green Group 151 A and B. Bracts acuminate to long-acuminate. Pedicel with 2 small bracts near base, green. Flowers are actinomorphic, 4-merous, bisexual.

*Calyx*.—4-merous, shallowly campanulate, white to light-yellow; broadly obovate; lobes free except at very base, 0.5-0.6 mm long, 1.0-1.2 mm wide; margin erose, hyaline.

*Corolla*.—4-merous, rotate.

*Gynoecium*.—1.5 mm high (including stigma), ovoid, light yellow in color; stigma sessile, fleshy, 4-lobed, 0.5 mm high, 1.0 mm wide. 1 pistil.

*Stamens*.—4, inserted in corolla lobe sinuses; filaments 1.0 mm long; anthers broadly sagittate (upside v-shaped), thecae lack pollen (non functional). Inflorescence emerges in late May to early June depending on temperature.

Fruit:

*Type*.—Berry containing 4 woody seeds — functional.

*Size*.—Rounded, approximately 3.5-4.5 mm diameter, with appressed sepals.

*Color*.—At maturity, fruit are glossy, closest to Black Group 202A.

*Environmental tolerance*.—Field grown plants of this new variety exhibit winter hardiness in U.S.D.A. Plant Hardiness Map (January 1990) Zone 6a (−10° F.). No insect or disease damage has been observed on plants growing in the field. Asexual reproduction by cuttings and grafts of our new variety have been accomplished in the vicinity of New Brunswick, N.J. The plant reproduces true to type in successive generations of asexual reproduction.

We claim:

1. A new and distinct variety of interspecific hybrid holly plant named 'CR-195-115', substantially as illustrated and described herein.

* * * * *